(12) United States Patent
Jones et al.

(10) Patent No.: US 6,802,851 B2
(45) Date of Patent: Oct. 12, 2004

(54) STENT ANEURYSM EMBOLIZATION METHOD USING COLLAPSIBLE MEMBER AND EMBOLIC COILS

(75) Inventors: Donald K. Jones, Lauderhill, FL (US); Vladimir Mitelberg, Aventura, FL (US)

(73) Assignee: Gordia Neurovascular, Inc., Miami Lakes, FL (US)

(*) Notice: Subject to any disclaimer, the term of this patent is extended or adjusted under 35 U.S.C. 154(b) by 0 days.

(21) Appl. No.: 09/957,323

(22) Filed: Sep. 20, 2001

(65) Prior Publication Data

US 2003/0055440 A1 Mar. 20, 2003

(51) Int. Cl.[7] .............................................. A61M 29/00
(52) U.S. Cl. ...................................................... 606/200
(58) Field of Search ................................. 606/151, 157, 606/158, 191, 192, 194, 195, 198, 200, 213, 215; 623/1.22, 1.11

(56) References Cited

U.S. PATENT DOCUMENTS

| | | |
|---|---|---|
| 4,512,338 A | 4/1985 | Balko et al. |
| 4,994,069 A | 2/1991 | Ritchart et al. |
| 5,411,550 A | 5/1995 | Herweck et al. |
| 5,527,338 A | 6/1996 | Purdy |
| 5,693,067 A | 12/1997 | Purdy |
| 5,749,894 A | 5/1998 | Engelson |
| 5,766,219 A | 6/1998 | Horton |
| 5,891,192 A | 4/1999 | Murayama et al. |
| 5,935,148 A * | 8/1999 | Villar et al. ............... 606/213 |
| 5,951,599 A * | 9/1999 | McCrory ................... 606/108 |
| 5,980,514 A * | 11/1999 | Kupiecki et al. ............ 606/32 |
| 6,036,720 A * | 3/2000 | Abrams et al. ............ 606/213 |
| 6,063,070 A * | 5/2000 | Eder .......................... 606/213 |
| 6,063,104 A | 5/2000 | Villar et al. |
| 6,063,111 A * | 5/2000 | Hieshima et al. .......... 606/191 |
| 6,086,577 A | 7/2000 | Ken et al. |
| 6,093,199 A * | 7/2000 | Brown et al. .............. 606/200 |
| 6,168,592 B1 | 1/2001 | Kupiecki et al. |
| 6,193,708 B1 * | 2/2001 | Ken et al. .................. 606/194 |
| 6,346,117 B1 | 2/2002 | Greenhalgh |
| 6,361,558 B1 | 3/2002 | Hieshima et al. |
| 6,383,174 B1 | 5/2002 | Eder |
| 6,454,780 B1 * | 9/2002 | Wallace ..................... 606/151 |

FOREIGN PATENT DOCUMENTS

| | | |
|---|---|---|
| EP | 1129666 A1 | 9/2001 |
| WO | WO 98/02100 A1 | 1/1998 |
| WO | WO 99/05977 A1 | 2/1998 |
| WO | WO 00/07524 A1 | 2/2000 |

* cited by examiner

*Primary Examiner*—David O. Reip
*Assistant Examiner*—Jessica R. Baxter
(74) *Attorney, Agent, or Firm*—Henry W. Collin

(57) ABSTRACT

A method and device used for treating an aneurysm of a patient. A framework for supporting one or more embolization elements is introduced into the patient's aneurysm. A stent, connected to the framework is introduced into a vessel leading into and communicating with the aneurysm, with the stent being compressed against the inner wall of the vessel for anchoring the framework. One or more embolization elements are introduced through the framework into the aneurysm, and in this manner the framework maintains the one or more embolization elements within the aneurysm. In the illustrative embodiment, the embolization element comprises an embolic coil, the stent comprises a helical coil, and the framework and helical coil are connected so as to be introduced into the patient simultaneously.

6 Claims, 3 Drawing Sheets

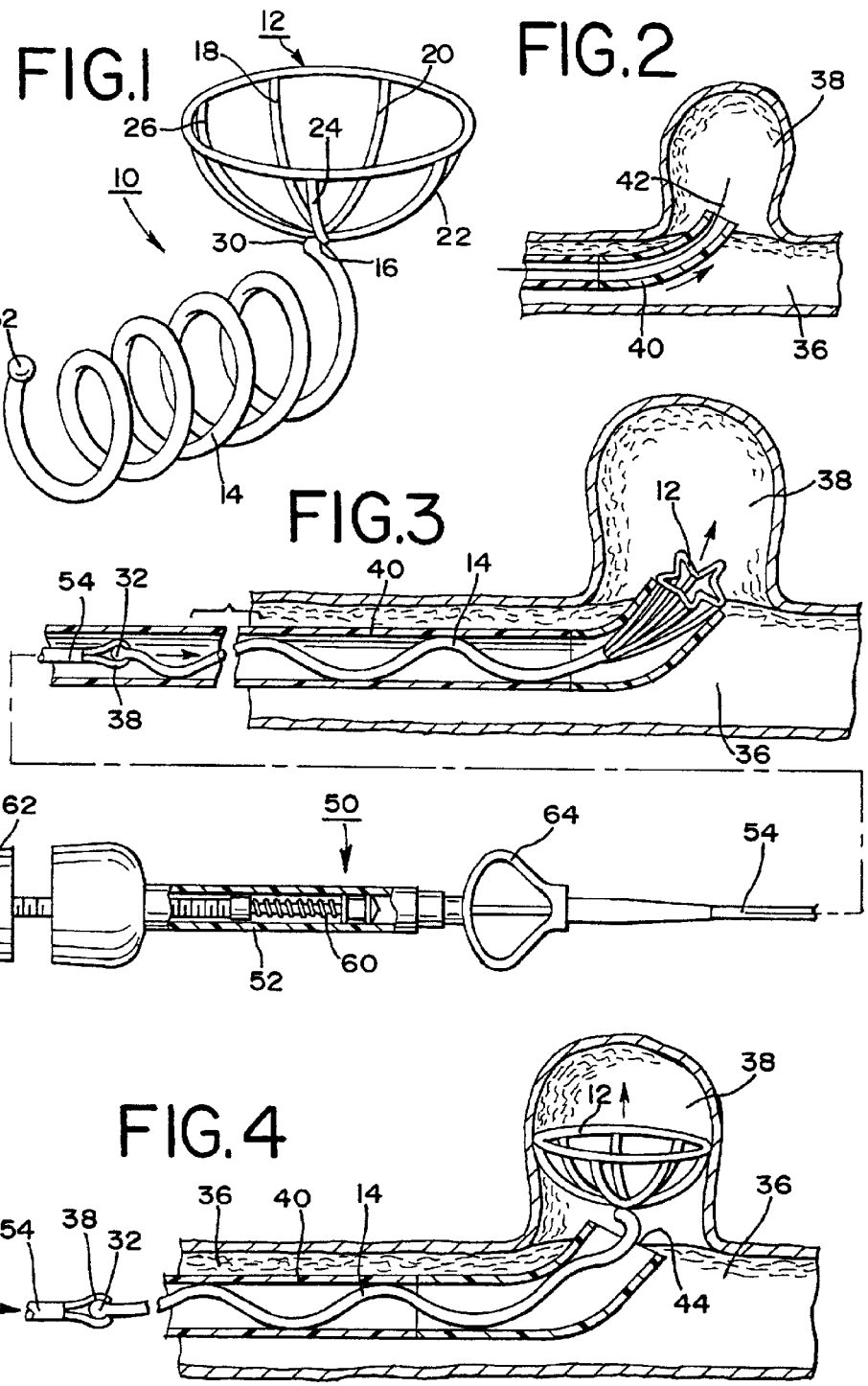

US 6,802,851 B2

STENT ANEURYSM EMBOLIZATION METHOD USING COLLAPSIBLE MEMBER AND EMBOLIC COILS

FIELD OF THE INVENTION

The present invention concerns a novel method and device for treating an aneurysm of a patient and, more particularly, a method and device in which an embolic device is maintained within the aneurysm.

BACKGROUND OF THE INVENTION

A well-known method of treating an aneurysm of a vessel wall includes the placement of a number of embolic coils within the aneurysm. Typically, a deployment device is used to introduce the coils, one by one, via a microcatheter, into the aneurysm. In wider neck aneurysms, it has been found that the embolic coils tend to migrate back to the parent vessel, which may result in occlusion of the parent vessel. Further, migration of the coil or coils back into the parent vessel may cause the coil or coils to be moved by the blood into another portion of the vessel, creating potentially serious problems.

It is, therefore, an object of the present invention to provide a method for maintaining an embolic device within an aneurysm.

Another object of the present invention is to provide a method that is relatively simple in operation for treating an aneurysm.

A still further object of the present invention is to provide a method for treating an aneurysm of a patient in which migration of the embolic device back into the parent vessel wall is prevented.

Another object of the present invention is to provide a vaso-occlusive device in which an embolization element is anchored within a patient's aneurysm.

Other objects and advantages of the present invention will become apparent as the description proceeds.

SUMMARY OF THE INVENTION

In accordance with the present invention, a method is provided for treating an aneurysm of a patient. The method comprises the steps of introducing into the patient's aneurysm a collapsible framework adapted to support an embolization element such as one or more embolic coils. A connected helical member is also introduced into the vessel leading to and communicating with the aneurysm, with the helical member being compressed against the inner wall of the vessel for anchoring the framework. An embolization element, such as one or more embolic coils, is introduced via a deployment device, through the framework and into the aneurysm.

A more detailed explanation of the invention is provided in the following description and claims, and is illustrated in the accompanying drawings.

BRIEF DESCRIPTION OF THE DRAWINGS

FIG. 1 is a perspective view of a vaso-occlusive device framework that can be used in accordance with the principles of the present invention;

FIG. 2 is a diagrammatic view of the introduction of a microcatheter;

FIG. 3 is a diagrammatic view of the introduction of a framework in accordance with the principles of the present invention;

FIG. 4 is a diagrammatic view, similar to a portion of FIG. 3, showing the framework that is expanded;

DETAILED DESCRIPTION OF THE ILLUSTRATIVE EMBODIMENT

Figure 5:
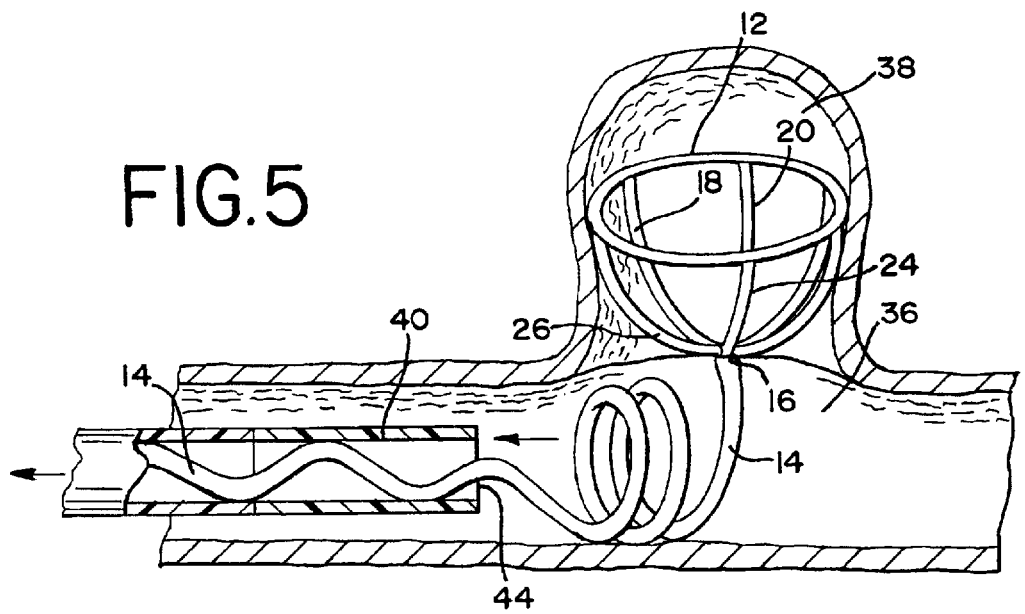
FIG. 5 is a diagrammatic view, similar to FIG. 4, but showing the framework as the microcatheter is being withdrawn.

Referring to FIG. 1, a vaso-occlusive device framework 10 is illustrated therein including framework element 12 and a stent 14 connected at the base 16 of framework element 12. The framework element 12 is a collapsible framework including struts 18, 20, 22, 24 and 26. Stent 14 is formed of a flexible wire that has been shaped into a cylindrical helix with its distal end 30 attached to the base 16 of framework element 12.

In the illustrative embodiment, the stent 14 is formed of a superelastic material in wire or tube form that will form and retain the helical configuration of the stent. A platinum coil is placed over the core to provide radiopacity and aid in the delivery of the device. The core wire is enlarged at the proximal end 32 and the distal end 30, to fill the lumen of the coil. This provides a method of restricting the movement of the core wire relative to the platinum coil. The ends of the core are then made atraumatic by beading or the like, as illustrated in FIG. 1. The assembly is then shaped using a die at a temperature and time sufficient for the assembly to retain the desired configuration. The shaped assembly is then placed in a fixture so that the framework element 12 can be attached. The stent may be attached to the base 16 of the framework element 12 by placing the framework element on the distal end 30 of the stent 14 and applying a small amount of UV curable adhesive to secure the framework element 12 to the stent 14.

A method of treating an aneurysm of a patient in accordance with the present invention is illustrated in FIGS. 2–11. Referring to FIG. 2, parent vessel 36 contiguous with aneurysm 38 is illustrated. As is known in the art with respect to treating an aneurysm, a microcatheter with guidewire 42 are introduced into the patient's vascular system so that the microcatheter, following the guidewire 42, is positioned with its distal end 44 being located at the mouth of the aneurysm. Guidewire 42 is withdrawn and vaso-occlusive device framework 10 is introduced as follows. Vaso-occlusive device framework 10 is inserted into the proximal end of microcatheter 40, with the framework element 12 being in a collapsed or folded condition so that it fits within the microcatheter. As illustrated in FIG. 3, a deployment device 50 is used for placing the vaso-occlusive device framework in the desired location. Although no limitation is intended, one example of a deployment device that can be used in connection with the present invention is disclosed in Hieshima U.S. Pat. No. 6,113,622, the disclosure of which is incorporated herein by reference. Deployment device 50 includes a hydraulic injector or syringe 52, coupled to the proximal end of a catheter 54. Bead 32 at the proximal end of stent 14 is disposed within the lumen of the distal end 58 of catheter 54. Bead 32 is tightly held within the lumen of distal section 58 until the deployment system is activated for release of the stent.

Syringe 52 includes a threaded piston 60 which is controlled by a handle 62. Catheter 54 includes a wing hub 64 which aids in the insertion of a catheter 54 into microcatheter 40.

Figure 6:
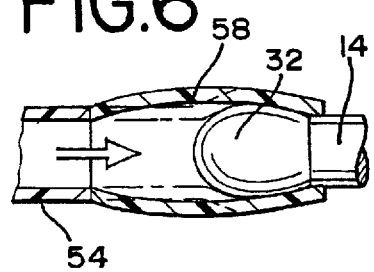
FIG. 6 is an enlarged cross-sectional view, partially broken, of the deployment device connected to the vaso-occlusive framework device.
Figure 7:
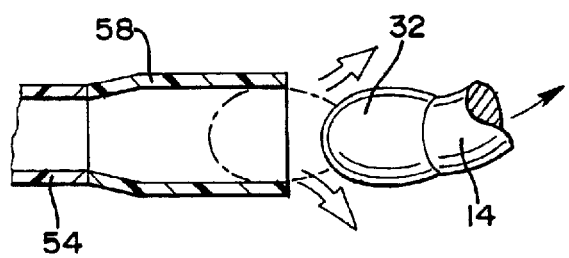
FIG. 7 is a view, similar to FIG. 6, but after the deployment device has been disengaged from the vaso-occlusive device framework.

As illustrated in FIG. 6, the distal end 58 is flexible, as disclosed in Hieshima U.S. Pat. No. 6,113,622, and tightly engages bead 32 of stent 14. However when handle 62 is activated to move the piston forward, as illustrated in FIG. 7 distal end 58 will expand by this hydraulic operation to release bead 32 and the stent and the framework device to which it is connected.

Figure 8:
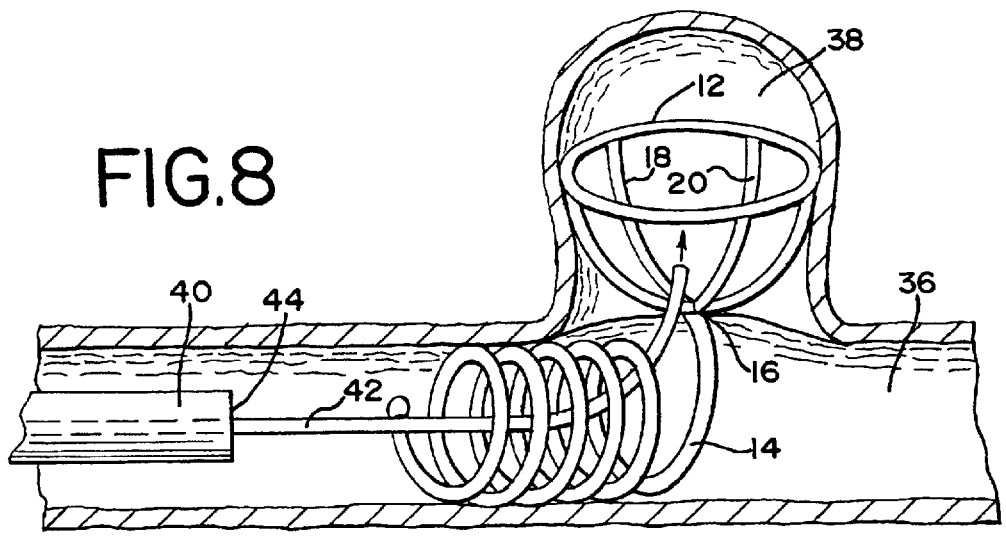
FIG. 8 is a diagrammatic view of the vaso-occlusive device framework of FIG. 1 in place within an aneurysm.

Now referring back to FIG. 4, it can be seen that vaso-occlusive device framework 10 has been moved forwardly through microcatheter 40 so that framework element 12 is located within aneurysm 38 and the framework element 12 has expanded to form a cup shaped element which substantially engages the inner walls of the aneurysm. Once the vaso-occlusive device framework is positioned as illustrated in FIG. 4, handle 62 is activated to release bead 32 from deployment device 50 and, as illustrated in FIG. 5, microcatheter 4 is withdrawn. As microcatheter 40 is withdrawn, the wire forming stent 14 will become released and spring into its coiled form, as illustrated in FIG. 8. FIG. 8 shows the vaso-occlusive device framework 12 fully delivered to the aneurysm with the stent 14 providing a radial force on the vessel to prevent movement and migration of the framework element 12. As illustrated in FIG. 8, the outer diameter of the helical coil which forms stent 14 engages the inner wall of the parent vessel and becomes compressed against the inner wall.

Figure 9:
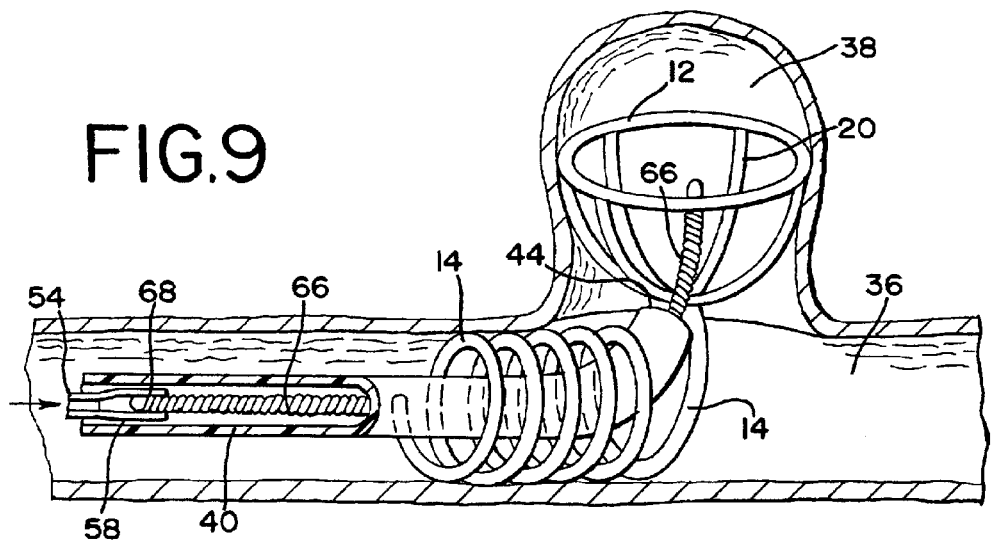
FIG. 9 is a diagrammatic view of an embolic coil being introduced through the framework into an aneurysm.
Figure 10:
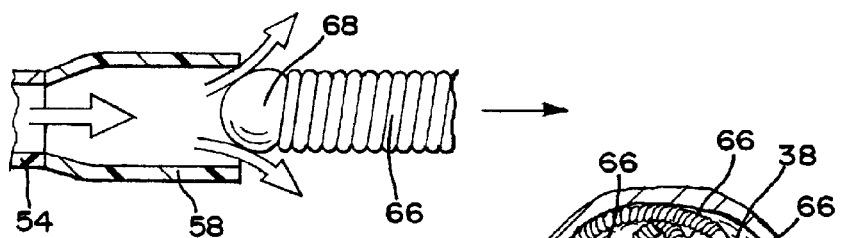
FIG. 10 is an enlarged cross-sectional view, partially broken, of the deployment device disconnecting from the embolic coil.

Once the framework is in place within the aneurysm, as illustrated in FIG. 8, the microcatheter 40 and guidewire 42 are again introduced into the patient's vessel 36, with guidewire 43 being fed through the lumen of helical coil/stent 14 and through the framework. Microcatheter 40 follows guidewire 42 so that the distal end 44 of microcatheter 40 is positioned adjacent an opening of the framework (see FIG. 9). Once the microcatheter is positioned adjacent the framework, guidewire 42 is withdrawn and deployment device 50, carrying an embolic coil 66, is used to place the embolic coils 66 within the framework inside the aneurysm 38. Referring to FIGS. 9 and 10, it is seen that distal end 58 of catheter 54 is tightly engaging the proximal end 68 of an embolic coil 66.

Embolic coil 66 is fed through microcatheter 40 into the aneurysm, as is known in the art except that the embolic coil 66 is fed through the framework which will serve to support the embolic coil once it is located within the aneurysm. Thus once the embolic coil is placed in the desired location within the aneurysm by pushing it with catheter 54 of deployment device 50, handle 62 of deployment device 50 is actuated to release embolic coil 66 from the distal end 58. Deployment device 50 is then withdrawn and distal end 58 of catheter 54 is then attached to proximal end 68 of another embolic coil 66. The next embolic coil 66 is fed into the aneurysm via a microcatheter 66 and through the framework. The desired number of embolic coils 66 are fed the same way, one after another, with the framework supporting the embolic coils and preventing the embolic coils from migrating from the embolism back into the parent vessel.

Embolic coils 66 may take various shapes and configurations but it is preferred that the embolic coils have a sufficient length and configuration to prevent them from migrating from the framework once they are inserted through the framework into the aneurysm. Coil 66 may take a helically wound form as shown or may be in the form of a random wound coil or any another equivalent configuration that would be suitable to aid in reducing or blocking the blood flow into the aneurysm.

Figure 11:
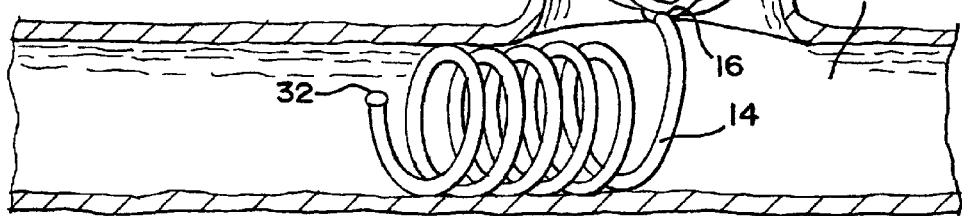
FIG. 11 is a diagrammatic view of the vaso-occlusive device, with the embolic coils in place within an aneurysm.

Once a suitable amount of embolic coils have been placed within the aneurysm and are supported by the framework, the microcatheter is withdrawn and stent 14 operates to support the framework and prevent migration of the framework back into the parent vessel, as illustrated in FIG. 11.

By utilizing stent 14 with a framework element 12, there is an improvement over a coil or stent alone in that the stent can provide more radial force on the vessel to prevent movement and migration of the framework element 12. This removes the necessity of requiring the framework element 12 to provide the radial force which would cause difficulty in delivering the device through the small lumen of a microcatheter and would also result in excessive pressure on the aneurysm wall.

The method of stent construction provides a method of stretch resistance without physically attaching the core wire to the proximal and distal ends of the coil. As the coil begins to stretch, it cinches on the head of the core wire and prevent further stretching.

The aneurysm framework element 12 provides a scaffolding on which tissue can grow, providing a treatment that is more efficacious then current treatments. The mesh or membrane 12 can carry a chemotherapeutic agent or may carry genetically engineered substances (cells/viral vectors). Framework element 12 may be made radiopaque using filters or chemically attached radiopaque substances such as iodine.

Although stent 14 is illustrated in the form of a helical coil, other equivalent shapes may be operable to prevent movement and migration of the aneurysm embolization element. Further, although the framework element 12 is shown with a generally cup shaped configuration, other equivalent configurations that are suitable for reducing or blocking flow into the aneurysm may be utilized. Although the deployment device 50 is illustrated as hydraulic, the detachment system can use other equivalent methods such as electrolytic, thermoadhesive or mechanical. Depending on the type of detachment the proximal end of the stent can be configure to couple as desired to the pusher.

Although an illustrative embodiment of the invention has been shown and described, it is to be understood that various other modifications and substitutions may be made by those skilled in the art without departing from the novel spirit and scope of the present invention.

What is claimed:

1. A method for treating an aneurysm of a patient, the aneurysm having a mouth that communicates with a vessel leading to the aneurysm, comprising the steps of:

introducing through the mouth and into the patient's aneurysm, a framework for supporting one or more embolization elements adapted to reduce or block the blood flow into the aneurysm, and to cause embolization;

said framework being adapted to be positioned within the aneurysm;

said embolization elements being adapted to be positioned within the aneurysm;

said introducing step including locating a stent, connected to said framework, in the vessel leading to and communicating with the aneurysm, with the stent being expanded against the inner wall of the vessel for anchoring the framework to a degree sufficient to prevent movement and migration of the framework, to avoid any excessive pressure on the aneurysm wall by the framework; and introducing one or more embolization elements through the framework into the aneurysm, wherein the framework maintains the one or more embolization elements within the aneurysm.

2. A method as defined in claim 1, in which the embolization element comprises an embolic coil.

3. A method as defined in claim 1, in which the stent comprises a helical coil.

4. A method as defined in claim 3, in which the coil further comprises a radiopaque coil overlying a core wire with enlarged ends restricting the movement of the core wire relative to the radiopaque coil.

5. A method as defined in claim 3, in which the helical coil has atraumatic ends.

6. A method as defined in claim 1, wherein the introducing steps include the steps of:

providing a deployment device for carrying and delivering the framework;

introducing the deployment device and the framework into the vessel of a patient via a catheter;

positioning the framework in a desired location in the embolism;

releasing the framework from the deployment device;

withdrawing the deployment device from the patient's vessel;

reintroducing a deployment device with an embolization element into the vessel of the patient, through the framework and into the aneurysm.

* * * * *

UNITED STATES PATENT AND TRADEMARK OFFICE
CERTIFICATE OF CORRECTION

PATENT NO. : 6,802,851 B2
DATED : October 12, 2004
INVENTOR(S) : Donald K. Jones et al.

It is certified that error appears in the above-identified patent and that said Letters Patent is hereby corrected as shown below:

<u>Title page,</u>
Item [73], Assignee,
"Gordia Neurovascular, Inc., Miami
  Lakes, FL (US)"
should read:
-- Cordis Neurovascular, Inc., Miami
  Lakes, FL (US) --.

Signed and Sealed this

Twenty-first Day of March, 2006

JON W. DUDAS
*Director of the United States Patent and Trademark Office*